United States Patent
Mosquera et al.

(10) Patent No.: US 12,324,772 B2
(45) Date of Patent: Jun. 10, 2025

(54) METHOD FOR CONTROLLING AN EYE SURGICAL LASER AND TREATMENT APPARATUS

(71) Applicant: SCHWIND eye-tech-solutions GmbH, Kleinostheim (DE)

(72) Inventors: Samuel Arba Mosquera, Aschaffenburg (DE); Nico Triefenbach, Mainaschaff (DE)

(73) Assignee: SCHWIND eye-tech-solutions GmbH, Kleinostheim (DE)

( * ) Notice: Subject to any disclaimer, the term of this patent is extended or adjusted under 35 U.S.C. 154(b) by 314 days.

(21) Appl. No.: 17/392,357

(22) Filed: Aug. 3, 2021

(65) Prior Publication Data

US 2022/0040001 A1   Feb. 10, 2022

(30) Foreign Application Priority Data

Aug. 4, 2020 (DE) .................... 10 2020 120 563.5
Jan. 20, 2021 (DE) .................... 10 2021 101 119.1

(51) Int. Cl.
*A61F 9/008* (2006.01)

(52) U.S. Cl.
CPC ........ *A61F 9/00827* (2013.01); *A61F 9/0084* (2013.01); *A61F 2009/00872* (2013.01)

(58) Field of Classification Search
CPC .. A61F 9/008; A61F 9/00814; A61F 9/00827; A61F 9/0084; A61F 2009/00872; A61F 2009/00897

(Continued)

(56) References Cited

U.S. PATENT DOCUMENTS

RE37,504 E      1/2002   Lin
9,233,025 B2 *  1/2016   Spooner .............. A61F 9/00827
(Continued)

FOREIGN PATENT DOCUMENTS

CN      1360486 A      7/2002
CN    101896144 A     11/2010
(Continued)

OTHER PUBLICATIONS

First Office Action issued Oct. 24, 2023 in Chinese Appl. No. 202110887060.X.

*Primary Examiner* — Ahmed M Farah
(74) *Attorney, Agent, or Firm* — MEDLER FERRO WOODHOUSE & MILLS PLLC

(57) ABSTRACT

A method for controlling a surgical laser for the separation of a volume body, with predefined posterior and anterior interfaces, from a human or animal cornea is disclosed. The method including controlling the laser by means of a control device such that it emits pulsed laser pulses in a shot sequence into the cornea. The interfaces are generated by the generation of a plurality of cavitation bubbles generated by photodisruption by means of an interaction of the individual laser pulses with the cornea. A minimum diameter of the volume body orthogonal to an optical axis of the volume body is determined depending on at least one diopter value for the volume body and on a preset thickness of the volume body viewed in a direction of the optical axis. A treatment apparatus, a computer program product and a computer-readable storage medium are also disclosed.

16 Claims, 2 Drawing Sheets

(58) Field of Classification Search
USPC .............................................. 606/4–5, 10–11
See application file for complete search history.

(56) References Cited

U.S. PATENT DOCUMENTS

| | | | |
|---|---|---|---|
| 11,890,232 B2* | 2/2024 | Arba Mosquera | A61F 9/00827 |
| 2004/0243112 A1 | 12/2004 | Bendett et al. | |
| 2007/0161972 A1 | 7/2007 | Felberg et al. | |
| 2008/0319428 A1 | 12/2008 | Wiechmann et al. | |
| 2012/0310224 A1* | 12/2012 | Miyagi | A61F 9/00827 606/5 |
| 2013/0110095 A1 | 5/2013 | Boxer Wachler | |
| 2016/0089270 A1* | 3/2016 | Fu | A61F 9/0084 606/5 |
| 2019/0110926 A1* | 4/2019 | Malek Tabrizi | A61F 9/00836 |
| 2019/0247225 A1 | 8/2019 | Stobrawa et al. | |
| 2021/0052423 A1* | 2/2021 | Arba-Mosquera | A61F 9/00825 |
| 2021/0169693 A1* | 6/2021 | Arba-Mosquera | A61F 9/00825 |
| 2021/0346198 A1* | 11/2021 | Arba Mosquera | A61F 9/00827 |
| 2021/0361486 A1* | 11/2021 | Arba Mosquera | A61F 9/009 |

FOREIGN PATENT DOCUMENTS

| | | | |
|---|---|---|---|
| CN | 108135742 A | 6/2018 | |
| CN | 110179581 A | 8/2019 | |
| CN | 110582255 A | 12/2019 | |
| DE | 102006053118 A1 | 5/2008 | |
| DE | 102011109058 A1 | 1/2013 | |
| EP | 1631223 B1 | 3/2006 | |

* cited by examiner

METHOD FOR CONTROLLING AN EYE SURGICAL LASER AND TREATMENT APPARATUS

The invention relates to a method for controlling an eye surgical laser for the separation of a volume body with a predefined posterior interface and a predefined anterior interface from a human or animal cornea and to a method for performing a surgical procedure on a human or animal cornea. Further, the invention relates to a treatment apparatus with at least one surgical laser for the separation of a volume body with predefined interfaces of a human or animal eye by means of photodisruption and with at least one control device for the laser or lasers. Furthermore, the invention relates to a computer program as well as to a computer-readable medium.

Opacities and scars within the cornea, which can arise by inflammations, injuries or congenital diseases, as well as a visual disorder such as for example myopia or hyperopia, impair the sight. In particular in case that these pathological and/or unnaturally altered areas of the cornea are located in the axis of vision of the eye, clear sight is considerably disturbed. In known manner, the thus altered areas are eliminated by a so-called phototherapeutic keratectomy (PTA) by means of an ablatively acting laser, for example an excimer laser. However, this is only possible if the pathological and/or unnaturally altered areas of the cornea are located in the superficial layers of the cornea. Areas located deeper, in particular within the stroma, are not reachable by means of ablative laser methods. Here, additional measures such as for example the exposure of the areas located deeper by means of an additional corneal incision have to be taken. By these additional measures, the treatment duration is disadvantageously considerably increased. In addition, there is the risk that further complications, such as for example the occurrence of inflammations, at the incision locations occur by the additional corneal incisions.

Further, it is known that in particular in removing lenticules, in particular in case of slight corrections, it can occur that upon the removal procedure of the volume body from the eye, it can break, whereby residues remain in the eye, whereby undesired refraction effects can in turn arise. Thus, it is of particular importance to remove the volume body from the eye as completely as possible to be able to realize a corresponding correction to the eye.

Therefore, it is the object of the present invention to provide a method and a treatment apparatus for controlling an eye surgical laser for the separation of the volume body with a predefined posterior interface and a predefined anterior interface from a human or animal cornea, and a method for performing a surgical procedure, by which the disadvantages of the prior art are overcome.

This object is solved by a method, a treatment apparatus, a computer program as well as a computer-readable medium according to the independent claims. Advantageous configurations with convenient developments of the invention are specified in the respective dependent claims, wherein advantageous configurations of the method are to be regarded as advantageous configurations of the treatment apparatus, of the computer program and of the computer-readable medium and vice versa.

A first aspect of the invention relates to a method for performing a surgical procedure on a human or animal cornea for the separation of a volume body from the cornea and to a method for controlling an eye surgical laser for the separation of a volume body with a predefined posterior interface and a predefined anterior interface from a human or animal cornea. The laser is controlled by means of a control device such that it emits pulsed laser pulses in a shot sequence into the cornea, wherein the interfaces are generated by the generation of a plurality of cavitation bubbles generated by photodisruption by means of an interaction of the individual laser pulses with the cornea. A minimum diameter of the volume body orthogonal to an optical axis of the volume body is determined depending on at least one diopter value for the volume body and on a preset thickness of the volume body viewed in a direction of the optical axis.

Thereby, for example in case of small optical corrections to the eye, it is allowed that a volume body is generated, which has the preset thickness, such that a breakage of the volume body is prevented upon an extraction of the volume body from the corneal volume. Thus, the volume body has a preset size and thickness, respectively, even in case of small corrections such that a breakage of the volume body upon the extraction is prevented. Further, it can be achieved by the method according to the invention that if the volume body should nevertheless break, only residues would remain at the edge of the lenticule, in particular in a transition zone, wherein the size of the intact extracted part of the volume body is sufficiently large to be able to reliably perform the corresponding correction to the eye.

In particular, the thickness maximum at a certain location of the volume body is to be understood by thickness of the volume body. In other words, the preset thickness is to be regarded where the volume body has its maximum thickness. For example, in myopic profiles, the preset thickness is assumed in the center of the volume body. In hyperopic profiles, the preset thickness is exactly at the edge of the optical zone of the volume body, but not at the edge of the volume body since the transition zone in turn connects them to each other. With cylindrical volume bodies, the thickness is not one point, but substantially a line, which extends centrally along the cylindrical axis. Also, in other shapes of the volume body, the preset thickness is to be regarded at the thickest location of the volume body. The preset thickness can also be referred to as preset depth. Alternatively, the thickness can also be referred to as extension, size, dimension, depth, width, length, extent, capacity, degree, strength, height, format, massiveness, gauge, order of magnitude, measure, extension, range, significance, content or intensity. Thus, the thickness can be defined such that it is a dimension or length, which is defined along an axis approximately perpendicular to the plane across the diameter, or the dimension or length along an axis approximately parallel to the optical or visual axis.

In particular, the minimum diameter is formed orthogonally to the optical axis or to the visual axis. The diameter can in particular be defined in that it is found where the two partial incisions, in other words the posterior interface and the anterior interface, join at the edge of the volume body. The diameter of the volume body is then formed between these two-dimensional locations.

In particular, a diopter value between −0.5 and −3 can be regarded as a slight correction. Preferably, a diopter value between −0.5 and −2 can be regarded as a slight correction. Again, particularly preferably, a diopter value between −0.5 and −1 can be regarded as a slight correction.

According to an advantageous form of configuration, a first diopter value is preset as the at least one diopter value for an optical zone of the volume body and/or a second diopter value is preset as the at least one diopter value for a transition zone of the volume body. Thus, it is allowed that the minimum diameter is determined depending on the different diopter values, either for the optical zone and/or the transition zone, wherein this can in particular be performed depending on the preset thickness such that a reliable extraction of the volume body from the corneal volume can be realized after the generation of the volume body.

It is further advantageous if a first diameter of the optical zone is determined depending on the first diopter value and a second diameter of the transition zone is determined depending on the second diopter value and the minimum diameter of the volume body corresponds to the greater one of the two diameters. Thus, the minimum diameter can be determined in simple manner such that a reliable extraction of the volume body from the corneal volume can be performed. For example, if the first diameter should be determined as greater than the second diameter, thus, the first diameter is preset as the minimum diameter. For example, if the second diameter should be determined as greater than the first diameter, thus, the second diameter is preset as the minimum diameter. The diameters to be determined are in particular absolute diameters.

In a further advantageous form of configuration of the method according to the invention, the second diopter value of the transition zone is determined with a preset first diameter of the optical zone and with a preset second diameter of the transition zone. Thus, it is allowed that the minimum diameter can be determined with different preset values. Thereby, it is allowed to a user that he can select from different values, whereby a highly flexible possibility is provided to be able to perform a correction to the eye and still be able to realize a reliable extraction of the volume body from the eye.

It is further advantageous if the second diopter value is determined with a preset first diopter value for determining the minimum diameter. Thereby, it is allowed that a user only has to preset the first diopter value, wherein the second diopter value is then automatically determined. Based on the first diopter value and the second diopter value, the minimum diameter can then be reliably determined on the condition of the minimum thickness of the volume body such that a reliable extraction of the volume body from the corneal volume can be realized.

It is also advantageous if a plurality of potential control data for controlling the eye surgical laser is proposed for selection to a user of the eye surgical laser on a display device of the eye surgical laser. Thus, it is in particular allowed that it is displayed to the user, which possibilities he has to generate the corresponding minimum diameter with the preset thickness under a certain specification of the user and still reliably perform the correction to the eye. For example, multiple thicknesses can also be proposed, wherein each of the proposed thicknesses is then greater than or at least equal to the minimum thickness. Thus, the user can select from a plurality of possibilities to be able to perform a corresponding correction. Thus, the user can select, under which conditions the volume body is to be generated in the corneal volume, whereby a breakage of the volume body can still be reliably prevented by the selection of the control data.

It is also advantageous if a value of greater than 20 μm, in particular at least 24 μm, is preset as a minimum value for the preset thickness of the volume body. In particular, it has turned out that a breakage of the volume body is prevented at 24 μm. For example, if a value of less than 20 μm should be selected, thus, the risk is increased that the volume body breaks upon extraction of the volume body in case of slight corrections.

It is further advantageous if the control data is generated for an eye surgical laser formed as a femto-laser in situ keratomileusis or for an eye surgical laser formed as a short incision lenticule extraction laser. In particular, a volume body can be generated by means of photodisruption based on these eye surgical lasers.

Further, it has proven advantageous if the control of the laser is performed considering the formula $$MLT = \max(\operatorname{abs}(S), \operatorname{abs}(C), \operatorname{abs}(S+C)) * \frac{OZ^2}{8*(n-1)} + ThicknessTZ$$

wherein S corresponds to a spherical diopter value, C corresponds to a cylindrical diopter value, OZ corresponds to a diameter of the optical zone of the volume body, n corresponds to a refractive index of the cornea, Thickness Tz corresponds to a thickness of a transition zone and MLT corresponds to the thickness of the volume body. Further, it can be provided that the thickness of the transition zone is determined by means of the formula:

$$ThicknessTZ = \max(\operatorname{abs}(STz), \operatorname{abs}(CTz), \operatorname{abs}(STz+CTz)) * \frac{TZ^2 - OZ^2}{8*(n-1)}$$

STz corresponds to a spherical diopter value of the transition zone, CTz corresponds to a cylindrical diopter value of the transition zone and Tz corresponds to a diameter of the transition zone of the volume body. In particular, it is provided that the diameter of the optical zone and the diameter of the transition zone are absolute diameters in the formulas. Based on the preset formulas, thus, the preset minimum thickness can be reliably determined with different specification conditions. In particular, the diameter, in particular the minimum diameter, of the volume body can be reliably determined, whereby a breakage of the volume body upon the extraction of the volume body from the corneal volume can be prevented. In particular, the thickness of the transition zone is defined at the location, at which the optical zone and the transition zone join.

It is further advantageous if the control of the laser is effected such that topographic and/or pachymetric and/or morphologic data of the cornea are taken into account. Thus, topographic and/or pachymetric measurements of the cornea to be treated as well as the type, the position and the extent of the for example pathological and/or unnaturally altered area within the stroma of the cornea as well as corresponding visual disorders of the eye can in particular be taken into account. In particular, control datasets are generated at least by providing topographic and/or pachymetric and/or morphologic data of the untreated cornea and providing topographic and/or pachymetric and/or morphologic data of the pathological and/or unnaturally altered area to be removed within the cornea or considering corresponding optical corrections for removing the visual disorders.

In a further advantageous form of configuration, the control of the laser is effected such that a transition zone is generated on the posterior interface such that the transition zone contacts the anterior interface, or the transition zone is generated on the anterior interface such that the transition zone contacts the posterior interface. Thereby, an additional incision can be prevented to connect the anterior interface to the posterior interface to generate the volume body. This is now effected via the transition zone, whereby a more effective generation of the volume body can be realized.

It is further advantageous if the control of the laser is effected such that the transition zone contacts the anterior interface or the posterior interface at an acute angle. Thereby, the volume body can be reliably generated and extracted without additional incision.

According to a further advantageous form of configuration, the control of the laser is effected such that the laser emits laser pulses in a wavelength range between 300 nanometers and 1400 nanometers, in particular between 700 nanometers and 1200 nanometers, at a respective pulse duration between 1 fs and 1 ns, in particular between 10 fs and 10 ps, and a repetition frequency of greater than 10 kHz, in particular between 100 kHz and 100 MHz. Such lasers are already used for photodisruptive methods in the eye surgery. The produced lenticule, which corresponds to the volume body, is subsequently removed via an incision in the cornea. The use of photodisruptive lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is ensured.

A second aspect of the invention relates to a treatment apparatus with at least one eye surgical laser for the separation of a volume body with predefined interfaces of a human or animal eye by means of photodisruption and with at least one control device for the laser or lasers, which is formed to execute the steps of the method according to the preceding aspect. In addition, the treatment apparatus includes a rotation scanner for predefined deflection of the laser beam of the laser towards the eye to be treated. The treatment apparatus according to the invention allows that disadvantages occurring in the use of usual ablative treatment apparatuses, namely relatively long treatment times and relatively high energy input by the laser into the cornea, are reliably avoided. These advantages are in particular achieved by the formation of the eye surgical laser as a photodisruptive laser.

Therein, the laser is suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz.

The treatment apparatus can also comprise a plurality, wherein plurality in particular means at least two, of control devices, which are then in turn formed to perform the method according to the invention.

In an advantageous form of configuration of the treatment apparatus, the treatment apparatus comprises a storage device for at least temporary storage of at least one control dataset, wherein the control dataset or datasets include control data for positioning and/or focusing individual laser pulses in the cornea, and includes at least one beam device for beam guidance and/or beam shaping and/or beam deflection and/or beam focusing of a laser beam of the laser. Therein, the mentioned control datasets are usually generated based on a measured topography and/or pachymetry and/or morphology of the cornea to be treated and/or the type of the pathologically and/or unnaturally altered area to be removed within the cornea and/or the visual disorder of the eye to be corrected.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including instructions causing the treatment apparatus according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and second inventive aspects, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

The Figures show the following.

In the figures, identical or functionally identical elements are provided with the same reference characters.

Figure 1:
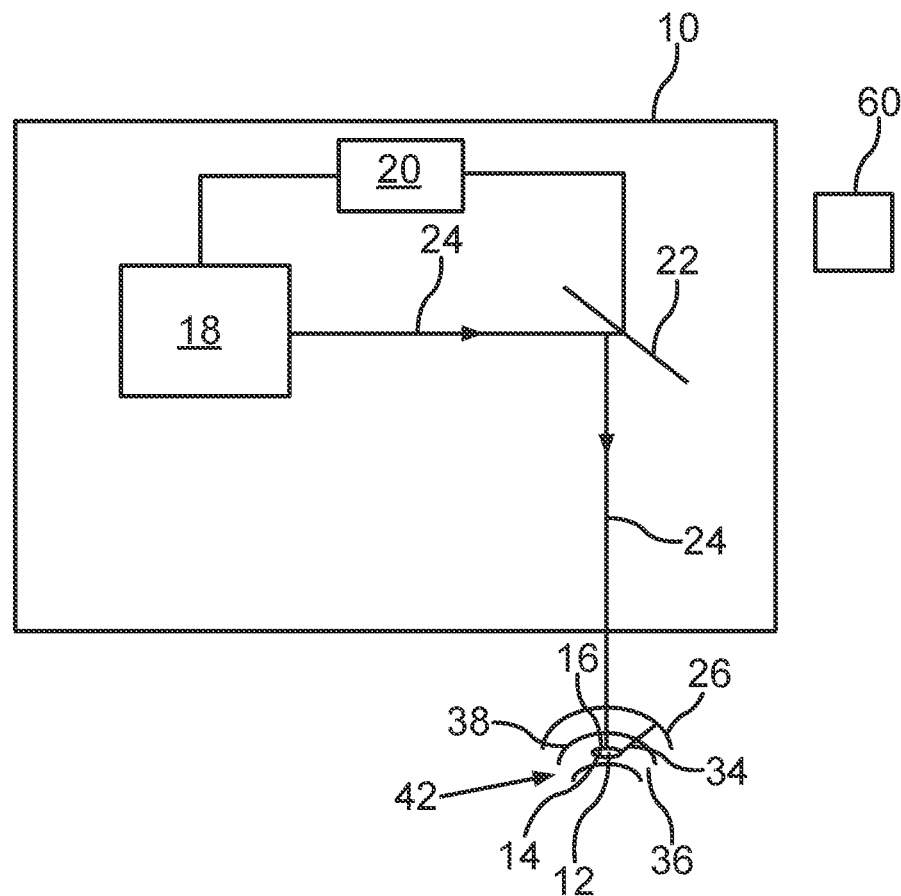
FIG. 1 is a schematic side view of an embodiment of a treatment apparatus.

FIG. 1 shows a schematic representation of a treatment apparatus 10 with an eye surgical laser 18 for the separation of a predefined corneal volume or volume body 12 with predefined interfaces 14, 16 in a cornea 44 (FIG. 3) of a human or animal eye 42 by means of photodisruption. One recognizes that a control device 20 for the laser 18 is formed besides the laser 18 such that it emits pulsed laser pulses for example in a predefined pattern into the cornea 44, wherein the interfaces 14, 16 of the volume body 12 to be separated are generated by the predefined pattern by means of photodisruption. The treatment apparatus 10 can also comprise further control devices. In the illustrated embodiment, the interfaces 14, 16 form a lenticular volume body 12, wherein the position of the volume body 12 is selected in this embodiment such that a pathological and/or unnaturally altered area 32 (see FIG. 2) within a stroma 36 of the cornea 44 is enclosed. Furthermore, it is apparent from FIG. 1 that the so-called Bowman's membrane 38 is formed between the stroma 36 and an epithelium 28.

Furthermore, one recognizes that the laser beam 24 generated by the laser 18 is deflected towards a surface 26 of the cornea by means of a beam device 22, namely a beam deflection device such as for example a rotation scanner. The beam deflection device is also controlled by the control device 20 to generate the mentioned predefined pattern in the cornea.

The illustrated laser 18 is a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz.

The control device 20 additionally comprises a storage device (not illustrated) for at least temporary storage of at least one control dataset, wherein the control dataset or datasets include control data for positioning and/or for focusing individual laser pulses in the cornea 44. The position data and/or focusing data of the individual laser pulses are generated based on a previously measured topography and/or pachymetry and/or the morphology of the cornea and the pathological and/or unnaturally altered area 32 for example to be removed or the optical visual disorder correction to be generated within the stroma 36 of the eye 42.

Figure 2:
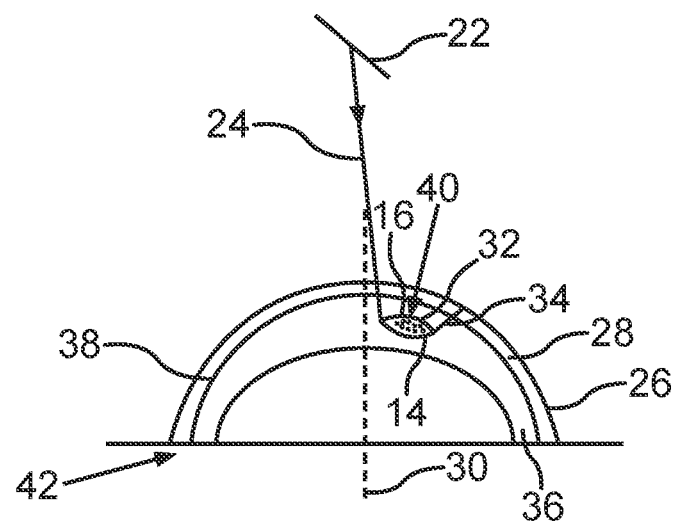
FIG. 2 is a further schematic side view of an embodiment of a treatment apparatus.

FIG. 2 shows a schematic diagram of the generation of the volume body 12 to be separated according to an embodiment of the present method. One recognizes that the interfaces 14, 16 are generated by means of the pulsed laser beam 24, which is directed towards the cornea 44 or towards the surface 26 of the cornea 44 via the beam deflection device 22. Therein, the interfaces 14, 16 form a lenticular volume body 12, which for example encloses the pathological and/or unnaturally altered area 32 within the stroma 36. Furthermore, the laser 18 generates a further incision 34 in the illustrated embodiment, which intersects the volume body 12 at a predefined angle and with a predefined geometry and is formed up to the surface 26 of the cornea 44. The volume body 12 defined by the interfaces 14, 16 can then be removed from the cornea 44 via the incision 34. In the illustrated embodiment, the pathological and/or unnaturally altered area 32 is formed within the stroma 36 and outside of an optical axis 30 of the eye 42.

In the illustrated embodiment, the interface 14, that is the interface located deeper in the eye 42 or the stroma 36, is first formed by means of the laser beam 24, wherein it then corresponds to the posterior interface 14. This can be effected by at least partially circularly and/or spirally guiding the laser beam 24 according to the predefined pattern. Subsequently, the interface 16 is generated in comparable manner, which then corresponds to the anterior interface 16, such that the interfaces 14, 16 form the lenticular volume body 12 (see also FIG. 1). Subsequently, the incision 34 is also generated by the laser 18. However, the order of the generation of the interfaces 14, 16 and of the incision 34 can also be changed.

Figure 3:
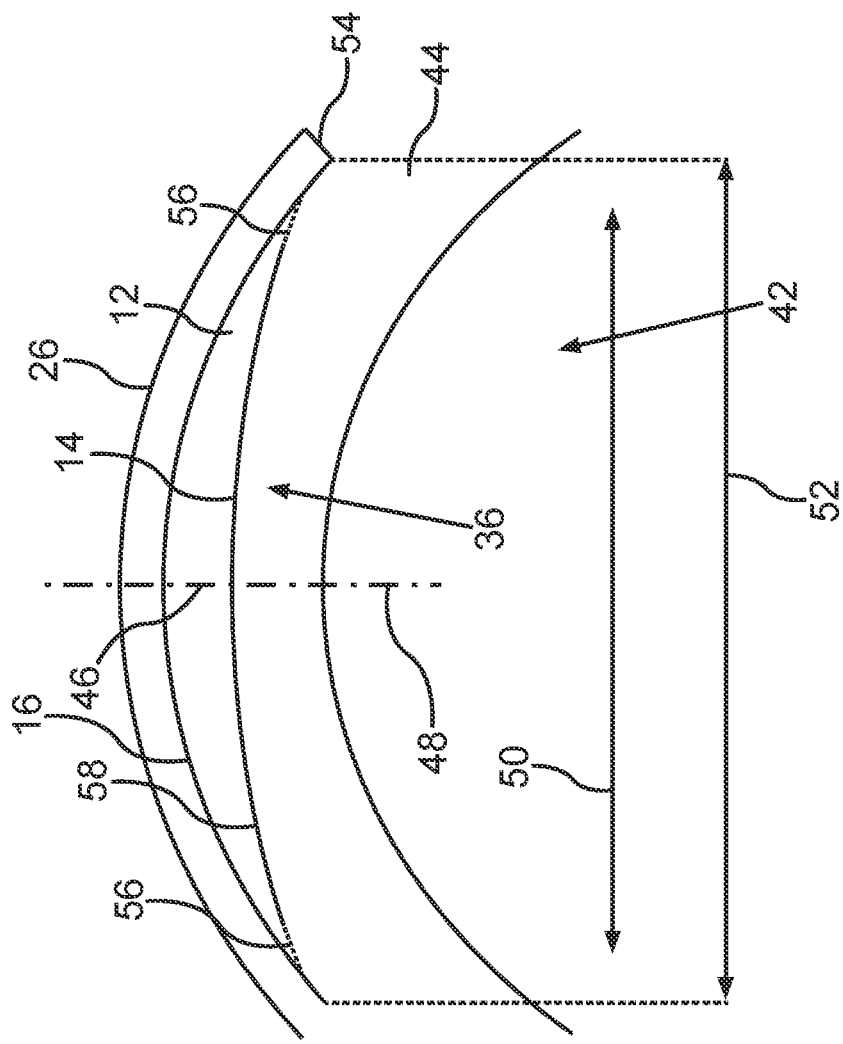
FIG. 3 is a schematic side view of an eye.

FIG. 3 shows a schematic side view of the eye 42, in particular, the cornea 44 is shown, wherein the cornea 44 in particular describes a corneal volume. In the present embodiment, the volume body 12 is in particular shown as a myopic profile. This in particular means that a preset thickness 46 of the volume body 12 is located in the center of the volume body 12. The preset thickness 46 of the volume body 12 is in particular formed viewed in the direction of an optical axis 48 of the volume body 12. Further, FIG. 3 shows that the volume body 12 can have a diameter 50 of the lenticule as well as a cap diameter 52 corresponding to a diameter of the upper incision, thus the anterior interface 16. Preferably, the cap diameter 52 is greater than the lenticule diameter. In particular, the volume body 12 is removed from the eye 42 via an incision 54, which corresponds to the incision 34 from FIG. 2.

In particular, it is provided that the laser 18 is controlled by means of the control device 20 such that it emits pulsed laser pulses in a shot sequence into the cornea 44, wherein the interfaces 14, 16 are generated by the generation of a plurality of cavitation bubbles 40 generated by photodisruption by means of an interaction of the individual laser pulses with the cornea 44, wherein a minimum diameter 50 of the volume body 12, which presently corresponds to the lenticule diameter, orthogonal to the optical axis 48 of the volume body 12 is determined depending on at least one diopter value for the volume body 12 and the preset thickness 46 of the volume body 12 viewed in a direction of the optical axis 48.

In the present embodiment, the anterior interface 16 in particular corresponds to a so-called upper incision and the posterior interface 14 corresponds to a lower incision. On the respective sides of the lower incision, presently thus of the posterior interface 14, there is a so-called transitions zone 56. An optical zone 58 is presently in particular formed on the posterior interface 14. In the present embodiment, thus, the optical zone 58 and the transition zone 56 form the posterior interface 14. Presently, the transition zone 56 contacts the anterior interface 14 presently at the respective outer edge thereof, preferably at an acute angle. Thus, an additional incision is not required to connect the anterior interface 16 to the posterior interface 14 and to form the extractable volume body 12.

In particular, it can be provided that a first diopter value is preset as the at least one diopter value for the optical zone 58 of the volume body 12 and/or a second diopter value is preset as the at least one diopter value for the transition zone 56 of the volume body 12. Further, a first diameter of the optical zone 58 can be determined depending on the first diopter value, and a second diameter of the transition zone 56 can be determined depending on the second diopter value, and the minimum diameter 50 then corresponds to the greater one of the two diameters.

Further, it can be provided that the second diopter value of the transition zone 56 is determined with a preset first diameter of the optical zone 58 and with a preset second diameter of the transition zone 56. Further, the second diopter value can be determined with a preset first diopter value for determining the minimum diameter 50.

Further, it can in particular be provided that a value of greater than 20 µm, in particular at least 24 µm, is preset as a minimum value for the preset thickness 46 of the volume body 12.

Furthermore, it can be provided that a plurality of potential control data for controlling the eye surgical laser 18 is proposed for selection to a user of the eye surgical laser 18 on a display device 60 (FIG. 1) of the eye surgical laser 18 or the treatment apparatus 10. For example, a following table can be displayed on the display device 60 for the user. Therein, the first table displays the first diameter of the optical zone 58, which should be selected greater than the value indicated in the table. In the first row, the preset minimum thickness 46 is registered. For example, the optical zone should have at least a first diameter of 5.2 mm with a diopter value of −3.0 and with a preset thickness 46 of 27 μm.

| Diopter value | Thickness 18 μm | Thickness 27 μm | Thickness 36 μm |
|---|---|---|---|
| −6.0 | 3.0 | 3.7 | 4.2 |
| −5.5 | 3.1 | 3.8 | 4.4 |
| −5.0 | 3.3 | 4.0 | 4.7 |
| −4.5 | 3.5 | 4.2 | 4.9 |
| −4.0 | 3.7 | 4.5 | 5.2 |
| −3.5 | 3.9 | 4.8 | 5.6 |
| −3.0 | 4.2 | 5.2 | 6.0 |
| −2.5 | 4.7 | 5.7 | 6.6 |
| −2.0 | 5.2 | 6.4 | 7.4 |
| −1.5 | 6.0 | 7.4 | 8.5 |
| −1.0 | 7.4 | 9.7 | 10.4 |
| −0.5 | 10.4 | 12.7 | 14.7 |

The second table shows the first diameter for the effective minimum optical zone 58 at the thicknesses 46 demonstrated in table 1, wherein it is limited by the limit values of 5.5 mm and 7.5 mm due to treatment restrictions.

| Diopter value | Eff. min OZ | Eff. min OZ | Eff. min OZ |
|---|---|---|---|
| −6.0 | 5.5 | 5.5 | 5.5 |
| −5.5 | 5.5 | 5.5 | 5.5 |
| −5.0 | 5.5 | 5.5 | 5.5 |
| −4.5 | 5.5 | 5.5 | 5.5 |
| −4.0 | 5.5 | 5.5 | 5.5 |
| −3.5 | 5.5 | 5.5 | 5.6 |
| −3.0 | 5.5 | 5.5 | 6.0 |
| −2.5 | 5.5 | 5.7 | 6.6 |
| −2.0 | 5.5 | 6.4 | 7.4 |
| −1.5 | 6.0 | 7.4 | 7.5 |
| −1.0 | 7.4 | 7.5 | 7.5 |
| −0.5 | 7.5 | 7.5 | 7.5 |

The third table in particular displays the determined minimum thickness 46 in mm, which would have to be used with the corresponding diopter values to achieve the desired correction and to consider the effective minimum optical zone 58.

| Diopter value | Thickness 18 μm | Thickness 27 μm | Thickness 36 μm |
|---|---|---|---|
| −6.0 | 60 | 60 | 60 |
| −5.5 | 55 | 55 | 55 |
| −5.0 | 50 | 50 | 50 |
| −4.5 | 45 | 45 | 45 |
| −4.0 | 40 | 40 | 40 |
| −3.5 | 35 | 35 | 36 |
| −3.0 | 30 | 30 | 36 |
| −2.5 | 25 | 27 | 36 |
| −2.0 | 20 | 27 | 36 |
| −1.5 | 18 | 27 | 28 |
| −1.0 | 18 | 19 | 19 |
| −0.5 | 9 | 9 | 9 |

The fourth table now shows the evaluation considering table three if a correction with the preset thickness 46 is possible.

| Diopter value | possible | possible | possible |
|---|---|---|---|
| −6.0 | yes | yes | yes |
| −5.5 | yes | yes | yes |
| −5.0 | yes | yes | yes |
| −4.5 | yes | yes | yes |
| −4.0 | yes | yes | yes |
| −3.5 | yes | yes | yes |
| −3.0 | yes | yes | yes |
| −2.5 | yes | yes | yes |
| −2.0 | yes | yes | yes |
| −1.5 | yes | yes | no |
| −1.0 | yes | no | no |
| −0.5 | no | no | no |

In particular, it is shown that not every correction is possible considering a preset thickness 46.

The tables 1 to 4 listed above are in particular generated based on the following formula. The control of the laser 18 is in particular effected considering the formula $$MLT = \max(\mathrm{abs}(S), \mathrm{abs}(C), \mathrm{abs}(S+C)) * \frac{OZ^2}{8*(n-1)} + ThicknessTZ$$

wherein S corresponds to a spherical diopter value, C corresponds to a cylindrical diopter value, OZ corresponds to a diameter of the optical zone 58 of the volume body 12, n corresponds to a refractive index of the cornea 44, Thickness Tz corresponds to a thickness of the transition zone 56 and MLT corresponds to the thickness 46 of the volume body 12.

Figure 4:
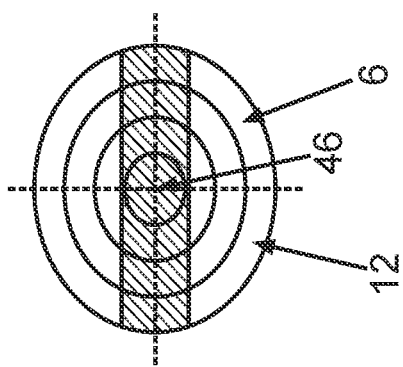
FIG. 4 is a schematic top view to a volume body.

FIG. 4 shows an embodiment of the volume body 12 to be removed in a schematic top view. In particular, the anterior interface 16 is shown. Presently, it is in particular shown that the volume body 12 has a cylindrical shape. Further, circular cavitation bubble paths are indicated. Here, it is in particular seen that the preset thickness 46 is substantially demonstrated along a line. Alternatively, other shapes of the volume body 12 can also be removed from the eye 42, in particular from the cornea 44. Therein, the preset thickness 46 always corresponds to the location with the maximum thickness of the volume body 12. In particular, it is thus provided that the minimum thickness 46 for this location is preset at the maximum thickness of the volume body 12. Herein, it is in particular to be ensured that in particular at least 20 μm, preferably at least 24 μm, are preset as the minimum thickness 46.

Further, it can in particular be provided that the first diopter value of the optical zone 58 is between −0.5 diopters and −12 diopters, typically −4 diopters. The second diopter value of the transition zone 56 is in particular between 0 diopters and −4 diopters, typically at approximately −2 diopters. The optical zone 58 typically has a first diameter between 5.5 mm and 7.5 mm, in particular for example 6.75 mm. The diameter of the transition zone 56, thus the second diameter, is in particular between 0 and 2.5 mm greater than the first diameter of the optical zone 58, typically greater by about 1.5 mm. The cap diameter 52 is for example at 6.5 to 9 mm, typically at 8 mm. A preset thickness of the cap, which is located between the surface 26 and the anterior interface 16, can for example be between 100 and 160 μm, typically about 120 μm. The incision 54 in particular has an angle between 45° and 135°, typically about 90°. The position of the incision 54 can be between 0° and 360°, typically at about 90°, wherein this is dependent on the eye, in particular depending on the fact if it is a left or right eye 42. The length of the incision 54 can for example be between 1.5 and 4 mm, typically about 3 mm.

What is claimed is:

1. A method for controlling an eye surgical laser for the separation of a volume body with a predefined posterior interface and a predefined anterior interface from a human or animal cornea, comprising:
controlling the laser by means of a control device such that it emits pulsed laser pulses in a shot sequence into the cornea, wherein the interfaces are generated by the generation of a plurality of cavitation bubbles generated by photodisruption by means of an interaction of the individual laser pulses with the cornea, wherein a minimum diameter of the volume body orthogonal to an optical axis of the volume body is determined depending on at least one diopter value for the volume body and on a preset thickness of the volume body viewed in a direction of the optical axis.

2. The method according to claim 1, wherein a first diopter value for an optical zone of the volume body is preset as the at least one diopter value and/or a second diopter value for a transition zone of the volume body is preset as the at least one diopter value.

3. The method according to claim 2, wherein a first diameter of the optical zone is determined depending on the first diopter value and a second diameter of the transition zone is determined depending on the second diopter value and the minimum diameter of the volume body corresponds to the greater one of the two diameters.

4. The method according to claim 2, wherein the second diopter value of the transition zone is determined with a preset first diameter of the optical zone and with a preset second diameter of the transition zone.

5. The method according to claim 2, wherein the second diopter value is determined with a preset first diopter value for determining the minimum diameter.

6. The method according to claim 1, wherein a plurality of potential control data for controlling the eye surgical laser is proposed for selection to a user of the eye surgical laser on a display device of the eye surgical laser.

7. The method according to claim 1, wherein a value of greater than 20 µm, in particular at least 24 µm, is preset as a minimum value for the preset thickness of the volume body.

8. The method according to claim 1, wherein control data is generated for an eye surgical laser formed as a femto laser in situ keratomileusis or for an eye surgical laser formed as a short incision lenticule extraction laser.

9. The method according to claim 1, wherein the control of the laser is performed considering the formula:

$$MLT = \max(\text{abs}(S), \text{abs}(C), \text{abs}(S+C)) * \frac{OZ^2}{8*(n-1)} + ThicknessTZ$$

wherein S corresponds to a spherical diopter value, C corresponds to a cylindrical diopter value, OZ corresponds to a diameter of the optical zone of the volume body, n corresponds to a refractive index of the cornea, Thickness Tz corresponds to a thickness of a transition zone and MLT corresponds to the preset thickness of the volume body.

10. The method according to claim 1, wherein the control of the laser is affected such that a transition zone is generated on the posterior interface such that the transition zone contacts the anterior interface or the transition zone is generated on the anterior interface such that the transition zone contacts the posterior interface.

11. The method according to claim 10, wherein the control of the laser is affected such that the transition zone contacts the anterior interface or the posterior interface at an acute angle.

12. The method according to claim 1, wherein the control of the laser is affected such that topographic and/or pachymetric and/or morphologic data of the cornea are taken into account.

13. The method according to claim 1, wherein the control of the laser is affected such that the laser emits laser pulses in a wavelength range between 300 nm and 1400 nm, in particular between 700 nm and 1200 nm, at a respective pulse duration between 1 fs and 1 ns, in particular between 10 fs and 10 ps, and a repetition frequency of greater than 10 kHz, in particular between 100 kHz and 10 MHz.

14. A treatment apparatus with at least one surgical laser for the separation of a volume body with predefined interfaces of a human or animal eye by means of photodisruption and with at least one control device, which is formed for controlling the laser according to a method of claim 1.

15. The treatment apparatus according to claim 14, wherein the control device comprises
at least one storage device for at least temporary storage of at least one control dataset, wherein the control dataset or datasets include control data for positioning and/or for focusing individual laser pulses in the cornea; and
at least one beam device for at least one of beam guidance, beam shaping, beam deflection, and beam focusing of a laser beam of the laser.

16. A non-transitory, computer-readable medium on which a computer program is stored, the computer program comprising instructions which cause a treatment apparatus with at least one surgical laser for separation of a volume body with predefined interfaces of a human or animal eye by means of photodisruption and with at least one control device to execute the method steps according to claim 1.

* * * * *